US005985288A

United States Patent [19]

Munson, Jr. et al.

[11] Patent Number: 5,985,288

[45] Date of Patent: Nov. 16, 1999

[54] **OUTER MEMBRANE PROTEIN P1 AND PEPTIDES OF *HAEMOPHILUS INFLUENZAE* TYPE B**

[75] Inventors: Robert S. Munson, Jr., Ballwin; Susan Grass, St. Louis, both of Mo.; Pele Chong, Thornhill, Canada; Yan-Ping Yang, Willowdale, Canada; Raafat Fahim, Mississauga, Canada; Dwo Yan Charles Sia, Thornhill, Canada; Patrick McVerry, Stroudsburg, Pa.; Michel Klein, Willowdale, Canada

[73] Assignee: Connaught Laboratories Limited, North York, Canada

[21] Appl. No.: 08/472,172

[22] Filed: Jun. 7, 1995

Related U.S. Application Data

[63] Continuation of application No. 07/849,411, filed as application No. PCT/CA90/00374, Oct. 31, 1990, abandoned.

[30] Foreign Application Priority Data

Oct. 31, 1989 [GB] United Kingdom ................... 8924473

[51] Int. Cl.[6] ................................................... A61K 39/102

[52] U.S. Cl. .................................... 424/256.1; 424/184.1; 424/185.1; 424/190.1; 424/234.1; 530/300; 530/324

[58] Field of Search ............................. 424/244.1, 193.1, 424/197.11, 234.1, 256.1, 184.1, 185.1, 190.1; 530/300, 324

[56] References Cited

U.S. PATENT DOCUMENTS

| | | |
|---|---|---|
| 4,496,538 | 1/1985 | Gordon . |
| 4,554,101 | 11/1985 | Hopp . |
| 4,673,574 | 6/1987 | Anderson . |
| 5,679,352 | 10/1997 | Chung et al. . |

FOREIGN PATENT DOCUMENTS

| | | |
|---|---|---|
| 0098581 | 8/1988 | European Pat. Off. . |
| 0276516 | 8/1988 | European Pat. Off. . |

OTHER PUBLICATIONS

Pongor et al, Methods in Enzymology, 154 450–473 (1987);.
Munson, R. et al (1988) Inf. Immun. 56: 2235–2242;.
Gonzales, F.R. et al, (1987) Inf. Immun. 55:2993–3000;.
Thomas, W.R., (1986) Inf. Immun. 52:812–817;.
Loeb, M.R. et al (1987) Inf. Immun. 55: 2612–2618;.
Hanson, M.S. et al (1989) Inf. Immun. 57 1639–1646;.
Granoff, D.M. et al (1986) J. Inf. Dis. 153: 448–461;.
Van Regenmortel, M.H.V. et al, (1989) Phil. Trans. R. Soc. Land. B323: 454–466;.
Lerner, R.A. et al (1983) in: The Biology of Immunologic Disease, F.J. Dixon & D.W. Fisher, eds. H.P. Publishing Co, N.Y., N.Y.pp. 331–338.
Barenkamp et al, J. Infect. Dis. 143: 668 (1981);.
Granoff et al, "*Haemophilus influenzae* epidemiology, immunology and prevention of disease"—Elsevier Publishing (1982);.
Inouye, M., personal communication.
Kyte and Doolittle, J. Mol. Biol. 157, 105, (1982);.
Masui, Y. et al, in "Experimental Manipulation of Gene Expression", Academic Press, 1983, pp. 15–32;.
Munson et al, Infect. Immun. 57, 3300, (1989);.
Thole et al, Infect. Immun. 56, 1633, (1988);.
Maniatis et al, Molecular Cloning; a Laboratory Manual, Cold Spring Harbour Press (1982);.
Marmur, J. Mol. Biol. 3, 208, (1961);.
Munson and Tolan, Infect. Immun. 57, 88, (1989);.
Proulx et al, submitted (1990);.
Silhavy et al, Experiments with gene fusion, Cold Spring Harbour Laboratory;.
Steward and Howard, Immunol. Today, 8, 57, (1987).
Kyte et al. J. Mol. Biol. 157:105–132, 1982.

*Primary Examiner*—Patricia A. Duffy
*Attorney, Agent, or Firm*—Sim & McBurney

[57] ABSTRACT

The gene for outer membrane protein P1 of *Haemophilus influenzae* b is expressed in *E. coli.* Methods for expression and demonstration of the immunogenicity of recombinant P1 and portions thereof are disclosed, along with an improved method for the purification of P1. The nucleotide sequence of the P1 gene and the derived amino acid sequence of the P1 protein of *Haemophilus influenzae* type b are disclosed and the methods used to determine the same. Also disclosed are the methods used to clone and express the P1 gene as well as the purification protocol for the P1 gene products (recombinant P1 and P1 fusion proteins). Fourteen peptides are synthesized corresponding to specific sequences of the mature P1 protein. The use of the P1 protein as n immunogens for immunization against the disease caused by *Haemophilus influenzae* type b and the use of the protein as a carrier for conjugation with an oligosaccharide derived from Haemophilus to generate a potentially efficacious vaccine against the disease, are described. Also disclosed is the use of P1 peptide-conjugates as immunizing agents to elicit anti-*Haemophilus influenzae* type b antibodies.

3 Claims, 11 Drawing Sheets

FIG.1A

```
1H  ATAGATTCGGGCTTTATAATTGCCCAGATTTTTATTTATAACAAAGGGTTCCAAATGAAA   60
                                                          Metlys   -21
3L                                                        ......
                                                          ......
6U                                                        ......
                                                          ......

1H  AAATTTAATCAATCTCTATTAGCAACTGCAATGTTGTTGGCTGCAGGTGGTGCAAATGCG   120
    LysPheAsnGlnSerLeuLeuAlaThrAlaMetLeuLeuAlaAlaGlyGlyAlaAsnAla   -1
3L  ...............A..........G.................................
    ...............Ile..........................................
6U  ...............A..........A.................................
    ...............Ile..........................................

1H  GCAGCGTTTCAATTGGCGGAAGTTTCTACTTCAGGTCTTGGTCGTGCCTATGCGGGTGAA   180
    AlaAlaPheGlnLeuAlaGluValSerThrSerGlyLeuGlyArgAlaTyrAlaGlyGlu   20
3L  .....................................................A......
    ............................................................
6U  ................................T..G........................
    ............................................................

1H  GCGGCGATTGCAGATAATGCTTCTGTCGTGGCAACTAACCCAGCTTTGATGAGTTTATTT   240
    AlaAlaIleAlaAspAsnAlaSerValValAlaThrAsnProAlaLeuMetSerLeuPhe   40
3L  .......................A..G.................................
    ............................................................
6U  ............................................................
    ............................................................
```

FIG.1B

```
1H  AAAACGGCACAGTTTTCCACAGGTGGCGTTTATATTGATTCTAGAATTAATATGAATGGT   300
    LysThrAlaGlnPheSerThrGlyGlyValTyrIleAspSerArgIleAsnMetAsnGly   60
3L  .................................G..........................
    .................................Val........................
6U  .................................G..........................
    .................................Val........................

1H  GATGTAACTTCTTATGCTCAGATAATAACAAATCAGATTGGAATGAAAGCAATAAAGGAC   360
    AspValThrSerTyrAlaGlnIleIleThrAsnGlnIleGlyMetLysAlaIleLysAsp   80
3L  .........G...C.            .T.GCAACT.C.AA......CT..GC....T..
    .........AlaSer            IleAlaThrThrLys...AsnSerAla...Tyr
6U  ......G..G...C.            .T...AGGTGC.AC......CA...C.......
    ......AlaAlaSer            IleLysGlyAlaThr...AsnThrThr......

1H  GGCTCAGCTTCACAGCGTAATGTTGTTCCCGGTGCTTTTGTGCCAAATCTTTATTTCGTT   420
    GlySerAlaSerGlnArgAsnValValProGlyAlaPheValProAsnLeuTyrPheVal   100
3L  ............G................T..............................
    ............Glu.............................................
6U  ............G................T..............................
    ............Glu.............................................

1H  GCGCCAGTGAATGATAAATTCGCGCTGGGTGCTGGAATGAATGTCAATTTCGGTCTAAAA   480
    AlaProValAsnAspLysPheAlaLeuGlyAlaGlyMetAsnValAsnPheGlyLeuLys   120
3L  ..T....A.....................C..A...........A...............
    ............................................................
6U  ..T.................A...G.......A...........A...............
    ..................Leu...Val.................................
```

FIG.1C

```
1H  AGTGAATATGACGATAGTTATGATGCTGGTGTATTTGGTGGAAAAACTGACTTGAGTGCT  540
    SerGluTyrAspAspSerTyrAspAlaGlyValPheGlyGlyLysThrAspLeuSerAla  140
    ............................A..............G.......C....
    ............................Ile....................Thr...
6U  ...A................................................C....
    ...Lys..............................................Thr...

1H  ATCAACTTAAATTTAAGTGGTGCTTATCGAGTAACAGAAGGTTTGAGCCTAGGTTTAGGG  600
    IleAsnLeuAsnLeuSerGlyAlaTyrArgValThrGluGlyLeuSerLeuGlyLeuGly  160
3L  ........................................C..................
    ...........................................................
6U  ........................................C..A...G...........
    ...............................................Val.........

1H  GTAAATGCGGTTTATGCTAAAGCCCAAGTTGAACGGAATGCTGGTCTTATTGCGGATAGT  660
    ValAsnAlaValTyrAlaLysAlaGlnValGluArgAsnAlaGlyLeuIleAlaAspSer  180
3L  ............................................A........A.....
    ............................................Ile......Asn...
6U  ............................................A.....A....G...
    ............................................Ile...ThrGlu...

1H  GTTAAGGATAACCAAATAACAAGCGCACTCTCAACACAGCAAGAACCATTCAGAGATCTT  720
    ValLysAspAsnGlnIleThrSerAlaLeuSerThrGlnGlnGluProPheArgAspLeu  200
3L  .....T....CA...G...A..CT.........GT..T.GC.CC....C...A..GG...
    ...Asn...Thr...ValLysThr.........ValLeuAlaPro...LeuLysGly...
6U  ......AT.GCA..       .A.......AA....   GT..TT...GGA.C.CCAA..
    ......IleAla...      Asn......Lys...   ValVal...GlyThrProIle
```

FIG.1D

```
1H  AAGAAGTATTTGCCCTCTAAGGACAAATCTGTTGTGTCATTACAAGATAGAGCCGCTTGG   780
    LysLysTyrLeuProSerLysAspLysSerValValSerLeuGlnAspArgAlaAlaTrp   220
3L  G.TC..A.............A................................A......
    AspGlnAsn...................................................
6U  CCTG.C......A......AA...G............................A......
    ProAsp......Thr......Asn....................................

1H  GGCTTTGGCTGGAATGCAGGTGTAATGTATCAATTTAATGAAGCTAACAGAATTGGTTTA   840
    GlyPheGlyTrpAsnAlaGlyValMetTyrGlnPheAsnGluAlaAsnArgIleGlyLeu   240
3L  ..G.............................................C...........
    ............................................................
6U  ..G........................................G....C...........
    ..........................................Gly...............

1H  GCCTATCATTCTAAAGTGGACATTGATTTTGCTGACCGCACTGCTACTAGTTTAGAAGCA   900
    AlaTyrHisSerLysValAspIleAspPheAlaAspArgThrAlaThrSerLeuGluAla   260
3L  ..T...........................A.............C......G........
    ..............................Thr..................Val......
6U  ..T...........................A.............C.........T.C...
    ..............................Thr.....................Tyr...

1H  AATGTCATCAAAGAAGGTAAAAAAGGTAATTTAACCTTTACATTGCCAGATTACTTAGAA   960
    AsnValIleLysGluGlyLysLysGlyAsnLeuThrPheThrLeuProAspTyrLeuGlu   280
3L  ....................................C.......................
    ....................................Leu.....................
6U  ....................................C..A....................
    ....................................LeuLys..................
```

FIG.1E

```
1H  CTTTCTGGTTTCCATCAATTAACTGACAAACTTGCAGTGCATTATAGTTATAAATATACC   1020
    LeuSerGlyPheHisGlnLeuThrAspLysLeuAlaValHisTyrSerTyrLysTyrThr   300
3L  ........G.....................T.............................
    ..............................Phe...........................
6U  ..............................T....T........................
    ..............................Phe...........................

1H  CATTGGAGTCGTTTAACAAAATTACATGCCAGCTTCGAAGATGGTAAAAAAGCTTTTGAT   1080
    HisTrpSerArgLeuThrLysLeuHisAlaSerPheGluAspGlyLysLysAlaPheAsp   320
3L  ..........................C..T.................G............
    ............................................................
6U  .............................T.................G............
    ............................................................

1H  AAAGAATTACAATACAGTAATAACTCTCGTGTTGCATTAGGGGCAAGTTATAATCTTTAT   1140
    LysGluLeuGlnTyrSerAsnAsnSerArgValAlaLeuGlyAlaSerTyrAsnLeuTyr   340
3L  .........................................................G..
    .........................................................Asp
6U  ........G.....................A..........................G..
    ..............................Ile........................Asp

1H  GAAAAATTGACCTTACGTGCGGGTATTGCTTACGATCAAGCGGCATCTCGTCATCACCGT   1200
    GluLysLeuThrLeuArgAlaGlyIleAlaTyrAspGlnAlaAlaSerArgHisHisArg   360
    ........A................................T..................
    ............................................................
6U  .........................................T..................
    ............................................................
```

FIG.1F

```
1H  AGTGCTGCAATTCCAGATACCGATCGCACTTGGTATAGTTTAGGTGCAACCTATAAATTC   1260
    SerAlaAlaIleProAspThrAspArgThrTrpTyrSerLeuGlyAlaThrTyrLysPhe   380
3L  ............................................................
    ............................................................
6U  .....................A......................G...............
    .....................Asn....................................

1H  ACGCCGAATTTATCTGTTGATCTTGGCTATGCTTACTTAAAAGGCAAAAAAGTTCACTTT   1320
    ThrProAsnLeuSerValAspLeuGlyTyrAlaTyrLeuLysGlyLysLysValHisPhe   400
3L  ............................................................
    ............................................................
6U  ............................................................
    ............................................................

1H  AAAGAAGTAAAAACAATAGGTGACAAACGTACATTGACATTGAATACAACTGCAAATTAT   1380
    LysGluValLysThrIleGlyAspLysArgThrLeuThrLeuAsnThrThrAlaAsnTyr   420
3L  ............................................................
    ............................................................
6U  .......C.C..CA.GCT.CA.GTGGCTTC         A.A.CA.....C........C
    ......AlaGlnGlnAlaAlaGlyGlyPhe         IleThr...............

1H  ACTTCTCAAGCACACGCAAATCTTTACGGTTTGAATTTAAATTATAGTTTCTAATCCGTT   1440
    ThrSerGlnAlaHisAlaAsnLeuTyrGlyLeuAsnLeuAsnTyrSerPhe            437
3L  ...................................................
    ...................................................
6U  ..............................C..A..C...............

1H  AAAAAATTTAGCATAATAAAGCACAATTCCACACTAAGTGTGCTTTTCTTTTATAAAACA   1500

1H  AGGCGAAAAATGACCGCACTTTATTACACTTATTACCCCTCGCCAGTCGGACGGCTTTTG   1560
```

FIG.5

Partial sequence of the P1 gene from strain MinnA (OMP subtype 1H)

```
AGTGCTGCAATTCCAGATACCGATCGCACTTGGTATAGTTTAGGTGCAACCTATAAATTC    1260
SerAlaAlaIleProAspThrAspArgThrTrpTyrSerLeuGlyAlaThrTyrLysPhe     380

                                   - > prSM793
ACGCCGAATTTATCTGTTGATCTTGGCTATGCTTACTTAAAAGGCAAAAAAGTTCACTTT    1320
ThrProAsnLeuSerValAspLeuGlyTyrAlaTyrLeuLysGlyLysLysValHisPhe     400

AAAGAAGTAAAAACAATAGGTGACAAACGTACATTGACATTGAATACAACTGCAAATTAT    1380
LysGluValLysThrIleGlyAspLysArgThrLeuThrLeuAsnThrThrAlaAsnTyr     420

ACTTCTCAAGCACACGCAAATCTTTACGGTTTGAATTTAAATTATAGTTTCTAATCCGTT    1440
ThrSerGlnAlaHisAlaAsnLeuTyrGlyLeuAsnLeuAsnTyrSerPhe              437
```

OUTER MEMBRANE PROTEIN P1 AND PEPTIDES OF *HAEMOPHILUS INFLUENZAE* TYPE B

This is a continuation of application Ser. No. 07/849,411 filed Jul. 7, 1992 now abandoned, which is a national stage filing of PCT/CA90/00374 filed Oct. 31, 1990.

FIELD OF INVENTION

The present invention relates to the outer membrane protein P1 obtained from *Haemophilus influenzae* type b. The gene for this protein, or modifications of this gene, when cloned in a suitable vector and expressed in a suitable host, gives proteins which retain some or all of the immunological properties of the native protein. Further, peptides based on the derived amino acid sequence of the P1 gene can be synthesized in vitro. These proteins and peptides can be used, with or without conjugation, as vaccines against the disease of *Haemophilus influenzae* type b. The proteins can also be conjugated with other haptens and polysaccharides and used as a T-cell dependent antigen and carrier.

BACKGROUND OF THE INVENTION

The disease caused by *Haemophilus influenzae* type b is a major cause of bacterial meningitis in children under the age of five years. Protective antibodies to the disease are induced by the capsular polysaccharide of the organism and a vaccine has been developed that utilizes the purified polyribosyl ribitol phosphate (PRP) as the antigen. This vaccine gave 90% protection in adults and in children over 24 months of age, but was ineffective in children under 24 months. Like other polysaccharide vaccines, the PRP does not induce the proliferation of T-helper cells, and re-immunization fails to elicit either booster response or increase in memory cells. A new conjugate vaccine has been developed that uses the PRP linked to diphtheria toxoid (see European Patent No. 0,098,581), which elicits T-cell dependent, booster responses and the production of PRP-specific IgG antibodies. To achieve broader protection in the 2 to 6 month age group and certain high risk groups, the incorporation of certain non-capsular antigens may be required. It has been shown that a monoclonal antibody directed against the outer membrane protein P1 of *Haemophilus influenzae* b has protective activity in the infant rat model of bacteremia. It has also been demonstrated that rabbit antisera directed against purified P1 also has protective activity in the rat model. The inventors have cloned, sequenced, and expressed in *E. coli,* the structural gene from P1 from three isolates.

Methods for inducing immunity against disease are constantly improving and there is presently a move towards the use of smaller and better defined materials as antigens. This is being undertaken to minimize or eliminate potential side-effects due to certain native immunogens, while preserving their immunogenicity and ability to confer protection against the disease.

SUMMARY OF INVENTION

The P1 gene, when expressed in an appropriate host/vector expression system, produces, according to one aspect of the invention, a protein product which when used as an immunogen induces antibodies reactive with the protein produced by *Haemophilus influenzae* type b. The inventors have further modified the gene to express a variety of protein analogues, in accordance with a further aspect of the invention, which retain some or all of the immunogenic properties of the protein produced by *Haemophilus influenzae* type b.

Because the P1 protein is a potentially protective antigen, it has been used by the inventors as part of a conjugate vaccine, in accordance with another aspect of the invention, wherein the hapten part of the conjugate is the capsular polysaccharide moiety of the Haemophilus organism. This avoids the problem of possible hyperimmunity to diphtheria when diphtheria toxoid is used as the carrier protein (see European Patent No. 0,098,581), and ensures better protection against the disease, especially in infants.

In addition, in accordance with a yet further aspect of the invention, the inventors have synthesized ten peptides with sequences corresponding to residues 60 to 88, 165 to 193, 189 to 218, 226 to 253, 248 to 283, 307 to 331, 339 to 370, 384 to 412 and 400 to 437 of mature P1, using solid-phase peptide synthesis, that are to be immunogenic and can act as antigens in a synthetic vaccine and as potential carriers in a conjugate vaccine, either alone or in combination.

The biosynthetic protein and peptide provided by the present invention also may be used in diagnostic kits for detection of the disease.

BRIEF DESCRIPTION OF DRAWINGS

FIG. 1 shows the DNA SEQ ID Nos: 1,2,3 and derived amino acid sequences SEQ ID Nos: 4,5,6 of the P1 genes from strain MinnA (OMP subtype 1H), strain 1613 (OMP subtype 3L), and strain 8358 (OMP subtype 6U). These data have previously been reported (Munson et al., Infect.Immun., 57 3300 (1989));

FIG. 5 shows the partial sequence (SEQ ID No: 11 Amino acid=SEQ ID No: 12 of the P1 gene from strain MinnA and the junction of the cro-lacZ fusion with the ompP1 gene in pRSM793. The fusion point is designated by the arrow; sequences 3' to the arrow are expressed as part of the fusion protein.

GENERAL DESCRIPTION OF INVENTION

Figure 2:
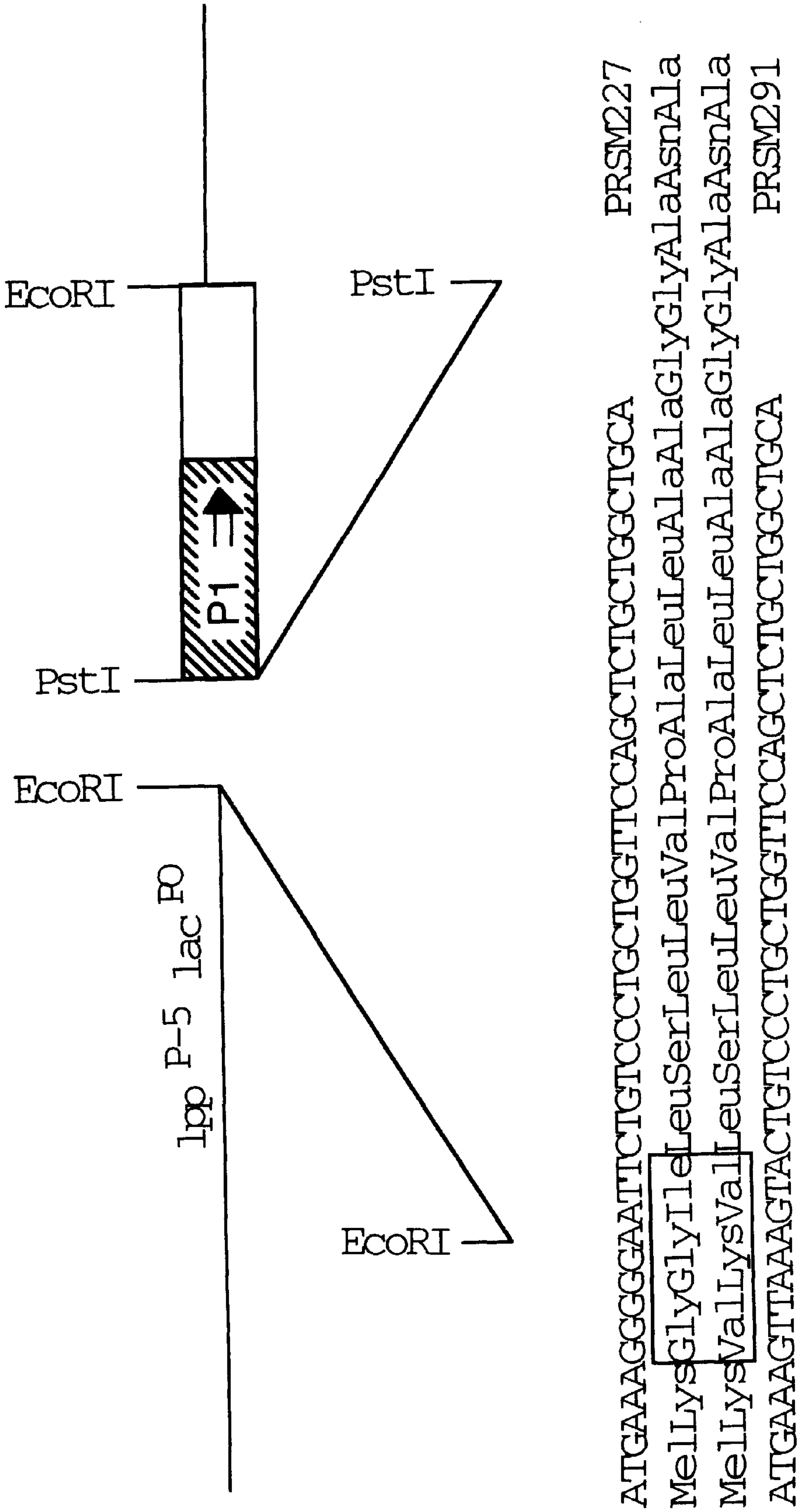
FIG. 2 shows the structure of two expression plasmids designed to generate recombinant P1. The vectors pINIIIA3 and a modification of this vector containing a consensus lpp promoter, described by Inouye and coworkers, was employed. This vector contains tandom promoters (lpp and lac). The P1 gene was subcloned from pRSM188, described by Munson and Grass (Infect.Immun., 56 2235 (1988)). The DNA SEQ ID Nos: 7,8 and derived amino acid sequence SEQ ID Nos: 8,9,10 synthetic leader peptides in pRSM227 and pRSM291 are shown. Details of the construction are given in Example I, below.
Figure 3:
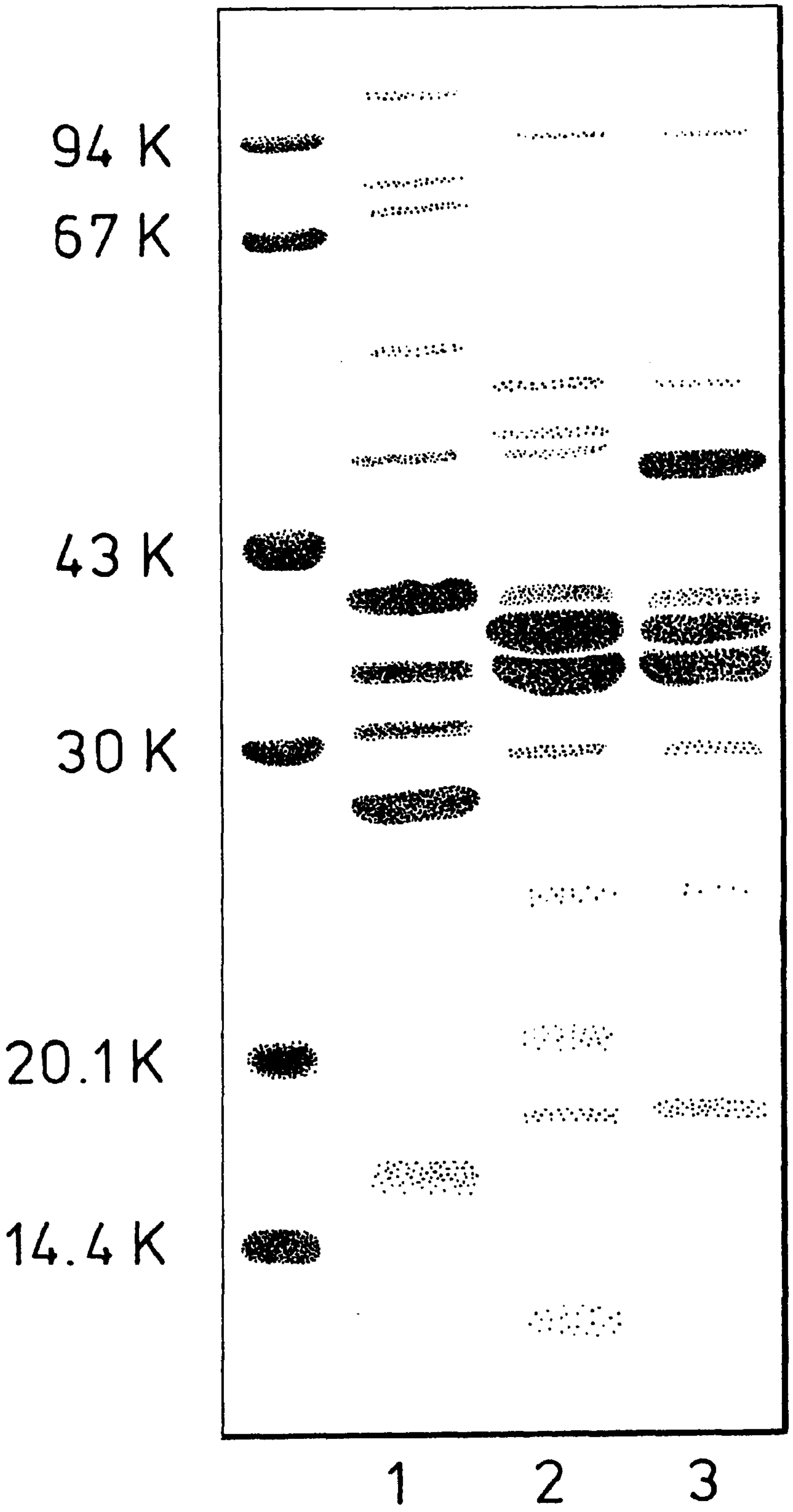
FIG. 3 shows a Coomassie-blue stained SDS PAGE gel of detergent-insoluble preparations enriched in outer membrane proteins. Lane 1 contains a preparation from *Haemophilus influenzae.* Lanes 2 and 3 contain preparations from *E. coli* not expressing and expressing P1, respectively. In further experiments, the ompA gene of *E. coli* has been mutated to remove the ompa protein from the outer membrane.

The gene coding for the outer membrane protein P1 from *Haemophilus influenzae* type b, strains MinnA, 1613 and 8358, were cloned, their nucleotide sequences being determined previously. Recombinant P1 and fusion proteins containing portions of P1 were produced in *E. coli.* Antisera prepared against the partially purified recombinant fusion proteins reacted with the P1 protein produced in *Haemophilus influenzae* b indicating that recombinant P1 and the fusion proteins induce antibodies which recognize native P1.

The gene, or fragments thereof, can be suitably expressed in *E. coli* under the control of other promoters, expressed in the absence of the leader peptide, or in other cloning systems. Expression in gram-positive bacteria expression systems, vaccinia virus, adenovirus, baculovirus, yeast, fungi, BCG or mammalian expression systems may be suitable alternative expression systems.

Purification of P1 has been reported by Munson and Grass (supra) and by Loeb (Infect.Immun., 55 2612 (1987)). Example III below details an improved purification for P1. This material has been employed for the synthesis of a conjugate vaccine. Haemophilus oligosaccharides (HPRP) were prepared by controlled acid hydrolysis and conjugated with the purified P1 protein using cyanogen bromide activation. The mean molecular size of the PRP molecule used for conjugation was determined to be approximately 20,000 Daltons. No linker molecule was used in the conjugation. The conjugate was tested for immunogenicity in rabbits and primary and secondary anti-PRP immune responses were observed (as set forth in Table 1 below). In addition, rabbit anti-PRP-P1 antisera showed a strong reaction against P1 in immunoblot analysis. This data indicates that P1 can be used as a carrier protein in a conjugate vaccine, thus avoiding the problem of possible hyperimmunity to diphtheria or tetanus when diphtheria or tetanus toxoids are used as the conjugation protein. In addition, PRP-P1 as a vaccine would possibly ensure a more consistent protection against *Haemophilus influenzae* type b disease, particularly in infants, as a result of homotypic protection provided by antibodies to the P1 protein.

Since antibodies against P1 are protective in the rat bacteremic model, the inventors decided to identify the immunodominant epitope(s) of P1 and generated probes to localize and characterize the P1 functional domains to be incorporated into a P1-based *Haemophilus influenzae* type b vaccine. Fourteen peptides were predicted to be hydrophilic in the Kyte-Doolittle plot (J.Mol.Biol., 157, 105 (1982)) of the P1 protein sequence and thus were chosen to be studied first (see Table 2 below). Synthetic peptides HIBP1-1 (residues 1 to 29 SEQ ID No: 13, HIBP1-2 residues 60 to 88 SEQ ID No: 14), HIBP1-3 (residues 103 to 137 SEQ ID No: 15), (HTBP1-4 (residues 165 to 193 SEQ ID No: 16), HIBP1 5 (residues 189 to 218 SEQ ID No: 17), HIBP1-6 (residues 226 to 253 SEQ ID No: 18), HIBP1-7 (residues 248 to 283 SEQ ID No: 19), HIBP1-8 (residues 279 to 312 SEQ ID No: 20), HIBP1-9 (residues 307 to 331 SEQ ID No: 21), NIBP1-10 (residues 339 to 370 SEQ ID No: 22), HIBP1-11 (residues 384 to 412 SEQ ID No: 23), HIBP1-12 (residues 39 to 64 SEQ ID No: 24), HIBP1-13 (residues 400 to 437 SEQ ID No: 25), and HIBP1-14 (residues 400 to 433 of 6U strain SEQ ID No: 26) were chemically synthesized with an additional cysteine at either the C- terminal end or the N-terminal end. The unique cysteine at one end of the peptide allows its coupling to the carrier protein in one specific orientation.

All synthetic peptides were assessed for their reactivity with antisera raised against native P1 in mice (six different strains) and guinea pigs in a peptide-specific ELISAS. As shown in Table 3 below, all murine anti-P1 antisera recognized HIBP1-3, HIBP1-7, HIBP1-9, and HIBP1-13 peptides very well, whereas guinea pig anti-P1 antisera recognized all the above peptides except HIBP1-13 in the same assays. This data indicates that major immunodominant B-cell epitopes of P1 are located within HIBP1-3 (residues 103 to 137 SEQ ID No: 15), HIBP1-7 (residues 248 to 283 SEQ ID No: 19), HIBP1-9 (residues 307 to 331 SEQ ID No: 21), and HIBP1-13 (400 to 437 SEQ ID No: 25).

To determine whether the synthetic peptides were possible vaccine candidates, free peptides and peptide-KLH conjugates were assessed individually for their immunogenicity. Rabbits were immunized and the anti-peptide antisera tested by ELISA, double immunodiffusion and immunoblot techniques. As shown in Table 4 below, all rabbit antisera except those raised against HIBP1-8 or HIBP1-8-KLH conjugate were shown to be monospecific for their respective immunizing peptides by ELISA. The induction of peptide-specific antibodies by free peptide indicates that the peptide comprises both T-helper determinant and B-cell epitope(s). In addition, anti-HIBP1-4, anti-HIBP1-5, anti-HIBP1-7, anti-HIBP1-9, anti-HIBP1-10, anti-HIBP1-11 and anti-HIBP1-14 antisera recognized P1 in all assays used, which indicates that these regions are exposed and free to interact with antibodies. Since these peptides contained potent T-helper determinant and peptide-KLH conjugates induced a strong antibody response in rabbits, it is obvious that they can act as antigens in a vaccine preparation.

EXAMPLES

Methods of molecular genetics, protein biochemistry, immunochemistry and hybridoma technology used but not explicitly described in this disclosure and these Examples are amply reported in the scientific literature and are well within the ability of those skilled in the art.

Example I

This Example shows the construction of an expression system designed to generate large quantities of recombinant P1.

The vector pINIIIA3 described by Inouye and coworkers was employed. This vector contains tandom promoters (lpp and lac). In this system, the expression of gene is controlled by the lactose regulatory system. For our construction, the P1 gene was cloned as a PstI to EcORI fragment from the plasmid pRSM188 described by Munson and Grass (supra) into the ECORI site of the vector. The leader peptide coding segment between the EcoRI site of the vector and the PstI site was reconstructed with synthetic oligonucleotides. This plasmid was designated pRSM227. Expression of P1 was further increased by: a) changing the lpp promoter to consensus (Inouye et al), b) site-directed mutagenesis to alter the sequence of the leader peptide, and c) cloning of a kanamycin cassette into the construct to stabilize the plasmid. The final construct is designated pRSM291. As synthesis of P1 was under the control of the lac regulatory system, P1 synthesis was induced by the addition of isopropyl-thiogalactoside to the culture media.

Example II

This Example illustrates the preparation of plasmids coding for the production of P1.

Figure 4:
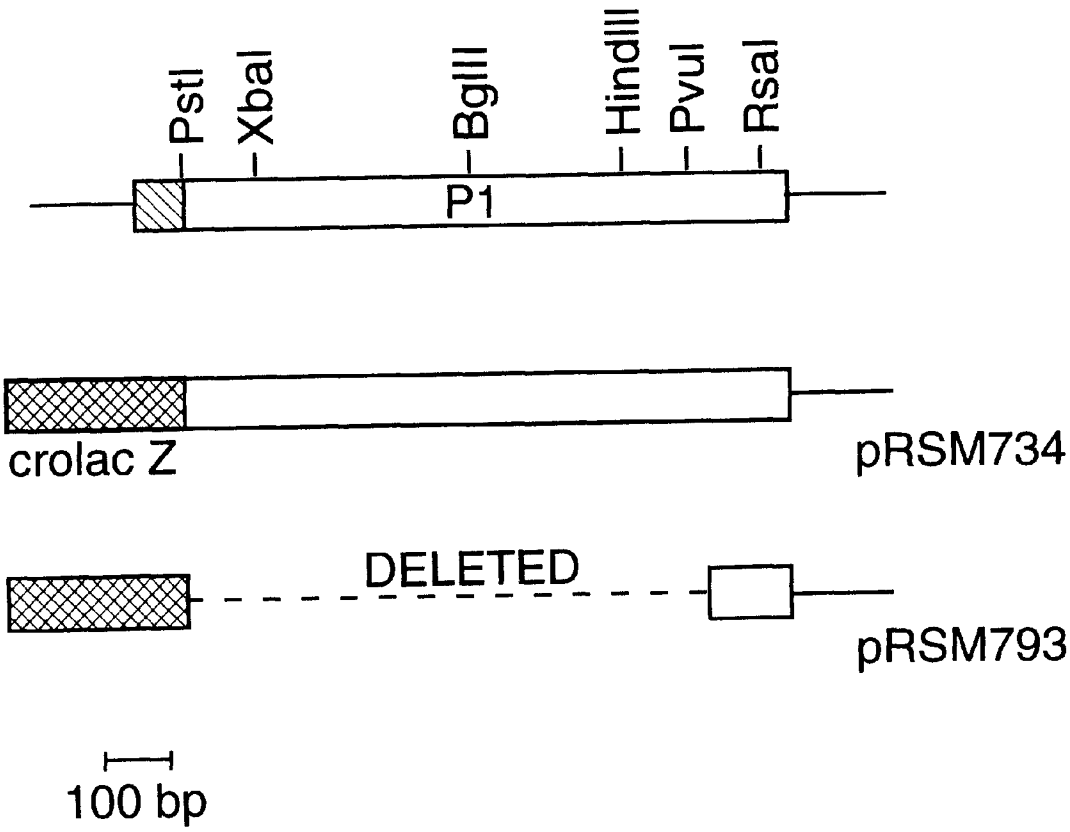
FIG. 4 shows a schematic of the P1 gene, a cro lacz ompP1 fusion gene in the vector pEX2 (pRSM734) and a gene fusion containing the 3' portion of the P1 gene (pRSM793). Details of the constructions are given Example II, below. The leader peptide coding sequences of the P1 gene are designated and the CRO-lacZ gene is designated.

A CRO-lacZ-ompP1 fusion gene was constructed in the vector pEX2. Plasmid pRSM188, containing the P1 gene, was digested with EcoRI at the site downstream of the P1 gene (see FIG. 2). The EcoRT ends were blunt-ended and the P1 gene was isolated as a PstI-EcoRI blunt ended fragment. This fragment was cloned into the pEX2 vector which had been sequentially digested with HindIII, blunt-ended and digested with PstI. The construct was designated pRSM734 (FIG. 4). A fusion protein containing all of the sequences of mature P1 is produced by *E. coli* pop 2136/pRSM734 after temperature shift to 42° C.

After removal of the XbaI site in pEX2, pRSM734 was digested with PstI and XbaI (XbaI cleaves once in the P1 gene) and digested with ExoIII. After blunt ending, ligation and transformation, a clone expressing only the 3' portion of the P1 gene as part of the fusion protein was isolated and characterized. The recombinant fusion was found to be recognized by rabbit or guinea pig P1-specific antisera in the immunoblot analyses. This plasmid was designated pRSM793 (see FIGS. 4 and 5).

Example III

This Example illustrates the purification of protein P1 from *Haemophilus influenzae* type b cultures.

Native P1 protein was purified from Cetavlon (0.1%) precipitates of the Eagen strain fermentation culture. Culture paste was homogenized in a polytron in the presence of 0.4M NaCl, and the suspension was allowed to stir for 2 hr. at room temperature. After centrifugation at 8,000 g for 30 min., the pellet was extracted with a buffer containing 10 mM EDTA/0.5% Triton/50 mM Tris-HCl, pH 8.0. This extraction preferentially solubilized P1 from the cell membrane. The crude P1 extract was further purified by ethanol precipitation, DEAE and hydroxylapitate chromatography. After these procedures, the P1 preparation was greater than 95% pure as judged by SDS PAGE analysis and scanning laser densitometry.

Example IV

This Example illustrates the preparation of the oligosaccharide/P1 conjugate.

Purified polysaccharide (PRP) from *Haemophilus influenzae* type b (U.S. Pat. No. 4,496,538) was heated to 80–90° C. for sufficient time to achieve a molecular size range of 20,000–2,000,000 Daltons as determined by gel filtration on a Sepharose CL-4B column.

A volume of the PRP was diluted to 25 mg/mL in 0.85% sodium chloride and the pH adjusted to 10.5 with 1 N NaOH. With stirring in an ice bath, a total of 0.1 volume of a concentrated solution of cyanogen bromide (10% w/v in 5 mM $NaHCO_3$, pH 10.8) was added. The pH was maintained between 10.0 and 11.0 by the addition of 1.0 N sodium hydroxide solution. Six minutes after the final addition, the pH of the reaction mixture was reduced to 6.0 with 1.0 N hydrochloric acid. The activated polysaccharide was purified by diafiltration against 0.85% sodium chloride at 4° C. to remove low molecular weight reactants. The PRP concentration was maintained at 25 mg/mL.

Purified P1 protein, at approximately 1 mg/mL, was dialyzed at 4° C. against 0.85% sodium chloride containing 0.5% Triton X-100 to remove Tris. One volume of dialyzed purified P1 protein, 0.1 volume of diafiltered, activated PRP and 0.1 volume of 1.0 M sodium bicarbonate were mixed together in a vessel that could be sealed. The pH was adjusted to 9.4 and the reaction mixture tumbled for 15–18 hours at 4° C. No attempt was made at this point to purify the conjugate away from unreacted protein or PRP. The polysaccharide and protein concentrations in the mixtures were determined by standard tests. The PRP-P1 conjugate was then used as immunogen in rabbit immunization. The immunogenicity of the PRP-P1 conjugate is shown in Table 1, below.

Example V

This Example illustrates the synthesis of peptides and the preparation of peptide carriers.

Peptides corresponding to the sequences of the mature P1 were synthesized in a commercial peptide synthesizer (see Table 2 below), and subsequently cleaved from the resin using hydrofluoric acid and purified by reverse-phase HPLC using a Vydac C4 column and a linear acetonitrile gradient (0–40%) in 0.1% trifluoracetic acid. All synthetic peptides used for immunogenicity studies were >95% pure as judged by HPLC analysis. The amino acid analyses of the peptide hydrolysates were in good agreement with their theoretical compositions.

Individual peptides were conjugated to KLH (keyhole limpet haemocyanin) or BSA (bovine serum albumin) at a 10:1 molar ratio of peptide over carrier protein by a standard method (Liu et al., Biochemistry, 18, 690, (1979)) with the following modification. The carrier protein was first modified with sulphosuccinimyl (4-iodoacetyl)-aminobenzoate (Sulfo-SIAB). The modified protein was further purified by gel filtration HPLC. The peptide was subsequently mixed with the modified protein carrier for 4–6 hrs, and the peptide-carrier conjugate isolated by gel filtration.

Example VI

This Example illustrates the protocols used to immunize animals and prepare antisera.

P1 protein-specific and peptide-specific antisera were prepared as follows. Rabbits, guinea pigs or mice were immunized intramuscularly with P1, PRP-P1 or individual peptide-KLH conjugates emulsified in complete Freund's adjuvant. Between 20 and 500 ug of the materials in 100–500 uL of phosphate-buffered saline (PBS) were used for each injection. The booster dose (half the amount of immunogen in incomplete Freund's adjuvant) was given in every two weeks. Blood was collected from the animals every two weeks after the first injection. Sera were separated from the clotted blood samples by centrifugation and heat inactivated at 56° C. for 30 minutes, then stored at −20° C.

Example VII

This Example illustrates the preparation of an ELISA specific for P1 peptides.

Individual P1 peptides (500 ng/well) were directly coated onto microtitre plates by incubation for 16 hrs. at 4° C. The wells were then blocked with 3% bovine serum albumin (BSA) in phosphate buffer saline, 7.4, (PBS) for 30 min. Serially diluted rabbit, guinea pig or mouse P1-specific to peptide-specific antisera were added to the wells and the plates incubated for 2 hrs. at room temperature. Excess antibody was removed by washing 3 times with wash buffer (0.1% Tween 20 in PBS). A commercial Protein A-alkaline phosphase conjugate was added to each well and the plates were further incubated at room temperature for 1 hr. After removal of the excess Protein A-peroxidase conjugate, the plates were washed 4 times with wash buffer and 0.2 mL of tetramethylbenzidine (TMB) substrate with $H_2O_2$ was added to each well. The plates were incubated in the dark until colour developed. The reaction was stopped by the addition of 50 uL of 1N sulphuric acid and the wells read in an ELISA reader at 450 nm. The results obtained are shown in Table 3, below.

Example VIII

This Example illustrates the use of the immunoblotting technique to characterize anti-P1 antisera.

Antibodies prepared in rabbits against the native protein P1, recombinant P1, synthetic KLH-peptide conjugates or PRP-P1 conjugates were tested for their specificity using the immunoblotting technique. Purified native P1 or recombinant P1 were electrophoresed and subsequently electrotransferred from an SDS-PAGE gel to a nitrocellulose strip, as described in the literature (Towbin et al., Proc.Natl.Acad.Sci., 76, 4350 (1979)). The nitrocellulose strips then were incubated for 2 to 4 hrs with appropriate dilutions of various rabbit antisera raised against native P1, recombinant P1, synthetic KLE-peptide conjugates or PRP-P1 conjugates. The antisera were diluted 1:500 with wash buffer (phosphate buffered saline containing 0.1% Triton X-100). Excess antibody was removed by washing 3 to 5 times with the wash buffer. Goat anti-rabbit IgG antibody conjugated to alkaline-phosphatase was purchased from a commercial source and used as the second antibody according to the manufacturer's instructions.

Example IX

This Example illustrates the preparation of Western blots.

A sarcosyl-insoluble preparation from *E. coli*/pRSM291 was employed to immunize mice. Three injections were administered; the first was administered with Freund's complete adjuvant and the subsequent two immunizations were administered with Freund's incomplete adjuvant. The CRO-lacZ-P1 fusion proteins were produced in *E. coli* strain pop 2136 containing pRSM734 or pRSM793 (see Example II above). The fusion proteins were purified by SDS-PAGE, and electroblotted to nitrocellulose. Mice were immunized subcutaneously twice by implantation of nitrocellulose strips containing the electroblotted immunogen.

Figure 6:
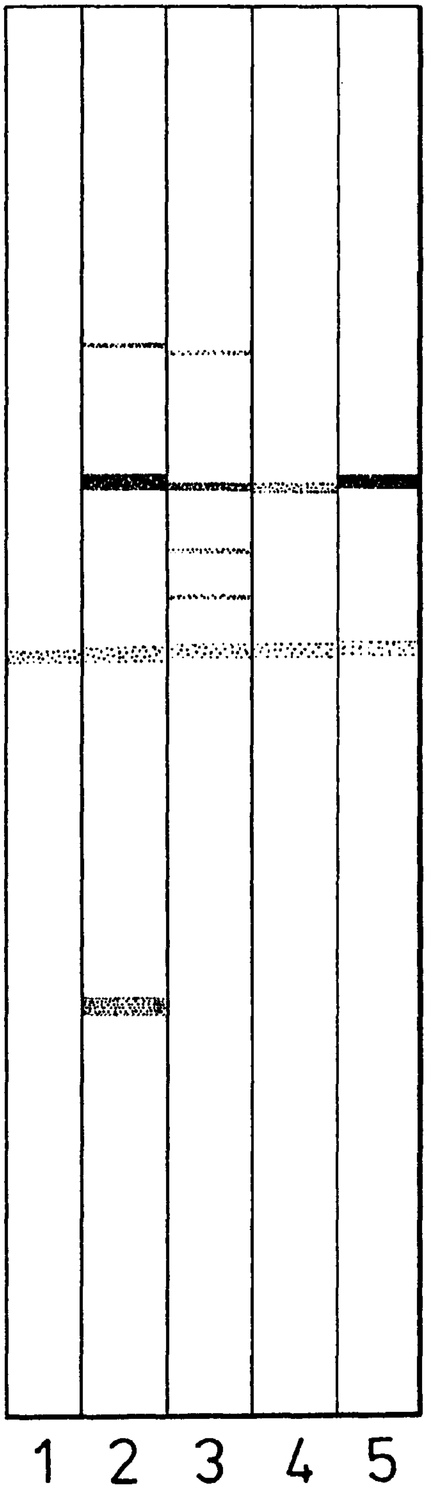
FIG. 6 shows a Western blot analysis of mouse monospecific antisera to recombinant P1 proteins. Mice were immunized with recombinant P1 or fusion proteins as detailed below and sera were tested for reactivity against P1 produced by Haemophilus. The method is given in Example IX, below. Lane 1, normal mouse sera obtained from mice from the same colony as the immunized mice; lane 2, antisera to recombinant P1; lane 3, antisera to the CRO-lacZ-P1 fusion protein produced by *E. coli*/pRSM734; lane 4, antisera to the CRO-lacZ-P1 fusion protein produced in *E. coli*/pRSM793; lane 5 is a positive control; the membrane was probed with tissue culture supernatants containing monoclonal anti-P1 antibodies.

Western blot analysis was performed by SDS-PAGE of a detergent-insoluble preparation of *Haemophilus influenzae* strain MinnA, electrotransfer to nitrocellulose, followed by sequential incubation with mouse antisera (pooled from 3 immunized mice, final dilution 1/100), and a goat anti-mouse IgG conjugated to alkaline phosphatase. The blot and development conditions were as described by Munson and Tolan (Infect.Immun., 57 88 (1989)). The results obtained are shown in FIG. 6.

SUMMARY OF DISCLOSURE

In summary of this disclosure, the P1 protein of *Haemophilus influenzae* type b has been produced recombinantly from the P1 gene, as have synthetic peptide corresponding to specific sequences of the mature P1 protein. These materials are useful in preparing vaccines against disease caused by the Haemophilus organism and in providing protein-oligosaccharide conjugates. Modifications are possible within the scope of this invention.

TABLE 1

IMMUNOGENICITY OF PRP-OMP CONJUGATE IN RABBITS

| | Prebleed | Post 1st Dose | Post 2nd Dose |
|---|---|---|---|
| GMT* (RIA Units) | <20 | <20 | 61 |
| No. animals with >4x rise in anti-PRP antibodies | N/A | 0/5 | 2/5 |

*GMT = Geometric mean of anti-PRP antibody units as determined by radio-immunoassay

TABLE 2

POTENTIAL T- AND B-CELL EPITOPES OF *Haemophilus influenzae Type b OUTER MEMBRANE PROTEIN P1*

| PEPTIDES | SEQUENCES | SEQ ID NO |
|---|---|---|
| HIBP1-1 (1–29) | *------HIBP1-1A------><br>AAFQLAEVSTSGLGRAYAGEAAIADNASV(C) | 13 |
| HIBP1-2 (60–88) | *---HIBP1-2A<br>GDVTSYAQIITNQIGMKAIKDGSASQRNV(C)<br>*----HIBP1-2B----> | 14 |
| HIBP1-3 (103–137) | *-----HIBP1-3A----><br>(C)VNDKFALGAGMNVNFGLKSEYDDSYDAGVFGGKTD<br>*----------HIBP1-3B----------> | 15 |
| HIBP1-4 (165–193) | *------HIBP1-4A-----><br>YAKAQVERNAGLIADSVKDNQITSALSTQ(C) | 16 |
| HIBP1-5 (189–218) | *----HIBP1-5A---><br>ALSTQQEFRDLKKYLPSKDKSVVSLQDRA(C) | 17 |
| HIBP1-6 (226–253) | *------HIBP1-6A--><br>(C)AGVMYQFNEANRIGLAYHSKVDIDFADR | 18 |

TABLE 2-continued

POTENTIAL T- AND B-CELL EPITOPES OF
*Haemophilus influenzae Type b OUTER MEMBRANE PROTEIN P1*

| PEPTIDES | SEQUENCES | SEQ ID NO |
|---|---|---|
| | *--HIBP1-7A--------> | |
| HIBP-7 | IDFADRTATSLEANVIKEGKKGNLTFTLPDYLELSG(C) | 19 |
| (248–283) | *--------HIBP1-7B--------------> | |
| | *-----HIBP1-8A-----> | |
| HIBP1-8 | LELSGFHQLTDKLAVHYSYKYTHWSRLTKLHASF(C) | 20 |
| (279–312) | *----------HIBP1-8B---------> | |
| | *------HIBP1-9A---> | |
| HIBP1-9 | KLHASFEDGKKAFDKELQYSNNSRV(C) | 21 |
| (307–331) | | |
| | *---------HIBP1-10A---> | |
| HIBP1-10 | LYEKLTLRAGIAYDQAASRHHRSAAIPDTDRT(C) | 22 |
| (339–370) | | |
| | *------HIBP1-11A---> | |
| HIBP1-11 | LSVDLGYAYLKGKKVHFKEVKTIGDKRTL(C) | 23 |
| (384–412) | | |
| HIBP1-12 | LFKTAQFSTGGVYIDSRINMNGDVTS(C) | 24 |
| (39–64) | | |
| | *----HIBP1- | |
| | 13B-------> | |
| HIBP1-13 | (C)FKEVKTIGDKRTLTLNTTANYTSQAHANLYGLNLNYSF | 25 |
| (400–437) | *--HIBP1-13A----> | |
| 1H | | |
| HIBP1-14 | (C)FKEAQQAAGGFITTTANYTSQAHANLYGLNLNYSF | 26 |
| (400–437) | ********** | |
| 6U | | |

TABLE 3

MOUSE STRAIN vs P1 PEPTIDES

| | Balb/C | | BL6 | | C3H | | A/J | | SWR/J |
|---|---|---|---|---|---|---|---|---|---|
| Peptide | 1 | 2 | 3 | 4 | 5 | 6 | 7 | 8 | 9 |
| p1-1 | < | < | < | < | < | < | 1600 | < | < |
| p1-2 | < | < | < | < | < | < | < | < | < |
| p1-3 | 6400 | 3200 | 1600 | 3200 | < | 3200 | 12800 | 6400 | 12800 |
| p1-4 | < | 6400 | < | < | < | < | 3200 | 1600 | < |
| p1-5 | 3200 | 6400 | 3200 | < | 3200 | 6400 | 6400 | < | < |
| p1-6 | < | < | < | < | < | < | 6400 | 6640 | 6400 |
| p1-7 | 51200 | 12800 | 12800 | 102400 | 1600 | 51200 | 51200 | 51200 | 800 |
| p1-8 | < | < | 400 | < | < | < | 800 | < | < |
| p1-9 | 6400 | 3200 | 6400 | 12800 | 12800 | 6400 | 1600 | 6400 | 1600 |
| p1-10 | 1600 | < | < | 3200 | < | < | 800 | 6400 | 3200 |
| p1-11 | < | < | < | 102400 | < | 25600 | 12800 | 25600 | 25600 |
| p1-12 | < | < | < | < | < | < | 3200 | < | < |
| p1-13 | 6400 | 6400 | 3200 | 51200 | 1600 | 25600 | 51200 | 102400 | 12800 |
| p1-13B | < | 400 | 800 | < | < | < | 1600 | 800 | 1600 |
| p1-14 | < | < | < | < | < | < | 800 | < | 800 |
| Native P1 | 102400 | 102400 | 102400 | 102400 | 51200 | 204800 | 204800 | 204800 | 102400 |

All numbers indicate reciprocal reactive titres
All reciprocal reactive titres calculated using normal mouse serum.
All antibody response are IgG + IgM
< = <1/200

TABLE 4

IMMUNOCHEMICAL PROPERTIES OF RABBIT ANTISERA RAISED AGAINST P1 PEPTIDES

| | ANTISERA REACTIVITY AGAINST | | |
|---|---|---|---|
| | SPECIFIC-ELISAs | | WESTERN BLOT |
| IMMUNOGEN | PEPTIDE | P1 | P1 |
| HIBP1-1 | YES | NO | YES |
| HIBP1-1-KLH | YES | NO | YES |
| HIBP1-2 | YES | NO | YES |
| HIBP1-2-KLH | YES | NO | YES |
| HIBP1-3 | YES | NO | YES |
| HIBP1-3-KLH | YES | NO | YES |
| HIBP1-4 | YES | YES | YES |
| HIBP1-4-KLH | YES | NO | YES |
| HIBP1-5 | YES | YES | YES |
| HIBP1-5-KLH | YES | YES | YES |
| HIBP1-6 | YES | NO | NO |
| HIBP1-6-KLH | YES | NO | NO |
| HIBP1-7 | YES | NO | YES |
| HIBP1-7-KLH | YES | YES | YES |
| HIBP1-8 | NO | NO | NO |
| HIBP1-8-KLH | NO | NO | NO |
| HIBP1-9 | YES | YES | YES |
| HIBP1-9-KLH | YES | NO | YES |
| HIBP1-10 | YES | NO | YES |
| HIBP1-10-KLH | YES | YES | YES |
| HIBP1-11 | YES | YES | YES |
| HIBP1-11-KLH | YES | YES | YES |
| HIBP1-12 | YES | NO | YES |
| HIBP1-12-KLH | YES | NO | YES |
| HIBP1-13 | YES | NO | YES |
| HIBP1-13-KLH | YES | NO | YES |
| HIBP1-14 | YES | YES | YES |
| HIBP1-14-KLH | YES | NO | YES |

References

1. Barenkamp et al. J. Infect. Dis., 143, 668, (1981)
2. Gonzales et al. Infect. Immun. 55, 2993, (1987)
3. Gordon, U.S. Pat. No. 4,496,538
4. Granoff et al., "*Haemophilus influenzae;* epidemiology, immunology and prevention of disease." Elsevier Publishing 1982
5. Granoff et al., J. Infect. Dis., 153, 448, (1986)
6. Inouye, M., personal communication
7. Kyte and Doolittle, J. Mol. Biol., 157, 105, (1982)
8. Loeb, Infect. Immun., 55 2612, (1987)
9. Masui, Y. et al. in "Experimental Manipulation of Gene Expression", Academic Press, 1983, page 15–32
10. Munson and Grass, Infect. Immun., 56, 2235, (1988)
11. Munson et al., Infect. Immun., 57, 3300, (1989)
12. Thole et al., Infect. Immun. 56, 1633, (1988)
13. Maniatis et al., Molecular cloning; a Laboratory manual, Cold Spring Harbour Press (1982)
14. Marmur, J. Mol. Biol., 3, 208, (1961)
15. Munson & Tolan, Infect. Immun. 57, 88, (1989)
16. Proulx et al., submitted (1990)
17. Silhavy et al., Experiments with gene fusion, Cold Spring Harbour Laboratory
18. Steward and Howard, Immunol. Today, 8, 57, (1987)

We claim:

1. A synthetic peptide which consists of an amino acid sequence of a portion of the P1 protein of *Haemophilus influenzae* type b and which contains at least one antigenic determinant of the P1 protein, the amino acid sequence being selected from the group consisting of amino acid residues 1 to 29 (SEQ ID No: 13), 60 to 88 (SEQ ID No: 14), 103 to 137 (SEQ ID No: 15), 165 to 193 (SEQ ID No: 16), 189 to 218 (SEQ ID No: 17), 226 to 253 (SEQ ID No: 18), 248 to 283 (SEQ ID No: 19), 279 to 312 (SEQ ID No: 20), 307 to 331 (SEQ ID No: 21), 339 to 370 (SEQ ID No: 22), 384 to 412 (SEQ ID No: 23), 400 to 437 (SEQ ID No: 25) and 400 to 433 (SEQ ID No: 26) of the P1 protein, as set forth in Table 2 for the MinnA strain.

2. A synthetic peptide which consists of an amino acid sequence of a portion of the P1 protein of *Haemophilus influenzae* type b and which contains an antigenic determinant which is a B-cell epitope of the P1 protein, the amino acid sequence being selected from the group consisting of amino acid residues 103 to 137 (SEQ ID No: 15), 248 to 283 (SEQ ID No: 19), 307 to 331 (SEQ ID No: 21), and 400 to 437 (SEQ ID No: 25) of the P1 protein as set forth in Table 2 for the MinnA strain.

3. A synthetic peptide which consists of an amino acid sequence of a portion of the P1 protein of *Haemophilus influenzae* type b and which contains an antigenic determinant contained in a surface exposed region of the P1 protein, the amino acid sequence being selected from the group consisting of amino acid residues 165 to 193 (SEQ ID No: 16), 189 to 218 (SEQ ID No: 17), 248 to 283 (SEQ ID No: 19), 307 to 331 (SEQ ID No: 21), 339 to 370 (SEQ ID No: 22), 384 to 412 (SEQ ID No: 23) and 400 to 433 (SEQ ID No: 26) of the P1 protein, as set forth in Table 2 for the MinnA strain.

* * * * *

```
                         SEQUENCE LISTING

(1) GENERAL INFORMATION:

   (iii) NUMBER OF SEQUENCES: 26


(2) INFORMATION FOR SEQ ID NO:1:

     (i) SEQUENCE CHARACTERISTICS:
          (A) LENGTH: 1560 base pairs
          (B) TYPE: nucleic acid
          (C) STRANDEDNESS: single
          (D) TOPOLOGY: linear

    (xi) SEQUENCE DESCRIPTION: SEQ ID NO:1:

ATAGATTCGG GCTTTATAAT TGCCCAGATT TTTATTTATA ACAAAGGGTT CCAAATGAAA      60

AAATTTAATC AATCTCTATT AGCAACTGCA ATGTTGTTGG CTGCAGGTGG TGCAAATGCG     120

GCAGCGTTTC AATTGGCGGA AGTTTCTACT TCAGGTCTTG GTCGTGCCTA TGCGGGTGAA     180

GCGGCGATTG CAGATAATGC TTCTGTCGTG GCAACTAACC CAGCTTTGAT GAGTTTATTT     240

AAAACGGCAC AGTTTTCCAC AGGTGGCGTT TATATTGATT CTAGAATTAA TATGAATGGT     300

GATGTAACTT CTTATGCTCA GATAATAACA AATCAGATTG GAATGAAAGC AATAAAGGAC     360

GGCTCAGCTT CACAGCGTAA TGTTGTTCCC GGTGCTTTTG TGCCAAATCT TTATTTCGTT     420

GCGCCAGTGA ATGATAAATT CGCGCTGGGT GCTGGAATGA ATGTCAATTT CGGTCTAAAA     480

AGTGAATATG ACGATAGTTA TGATGCTGGT GTATTTGGTG GAAAAACTGA CTTGAGTGCT     540
```

-continued

```
ATCAACTTAA ATTTAAGTGG TGCTTATCGA GTAACAGAAG GTTTGAGCCT AGGTTTAGGG    600

GTAAATGCGG TTTATGCTAA AGCCCAAGTT GAACGGAATG CTGGTCTTAT TGCGGATAGT    660

GTTAAGGATA ACCAAATAAC AAGCGCACTC TCAACACAGC AAGAACCATT CAGAGATCTT    720

AAGAAGTATT TGCCCTCTAA GGACAAATCT GTTGTGTCAT TACAAGATAG AGCCGCTTGG    780

GGCTTTGGCT GGAATGCAGG TGTAATGTAT CAATTTAATG AAGCTAACAG AATTGGTTTA    840

GCCTATCATT CTAAAGTGGA CATTGATTTT GCTGACCGCA CTGCTACTAG TTTAGAAGCA    900

AATGTCATCA AAGAAGGTAA AAAAGGTAAT TTAACCTTTA CATTGCCAGA TTACTTAGAA    960

CTTTCTGGTT TCCATCAATT AACTGACAAA CTTGCAGTGC ATTATAGTTA TAAATATACC   1020

CATTGGAGTC GTTTAACAAA ATTACATGCC AGCTTCGAAG ATGGTAAAAA AGCTTTTGAT   1080

AAAGAATTAC AATACAGTAA TAACTCTCGT GTTGCATTAG GGGCAAGTTA TAATCTTTAT   1140

GAAAAATTGA CCTTACGTGC GGGTATTGCT TACGATCAAG CGGCATCTCG TCATCACCGT   1200

AGTGCTGCAA TTCCAGATAC CGATCGCACT TGGTATAGTT TAGGTGCAAC CTATAAATTC   1260

ACGCCGAATT TATCTGTTGA TCTTGGCTAT GCTTACTTAA AAGGCAAAAA AGTTCACTTT   1320

AAAGAAGTAA AAACAATAGG TGACAAACGT ACATTGACAT TGAATACAAC TGCAAATTAT   1380

ACTTCTCAAG CACACGCAAA TCTTTACGGT TTGAATTTAA ATTATAGTTT CTAATCCGTT   1440

AAAAAATTTA GCATAATAAA GCACAATTCC ACACTAAGTG TGCTTTTCTT TTATAAAACA   1500

AGGCGAAAAA TGACCGCACT TTATTACACT TATTACCCCT CGCCAGTCGG ACGGCTTTTG   1560
```

(2) INFORMATION FOR SEQ ID NO:2:

(i) SEQUENCE CHARACTERISTICS:
(A) LENGTH: 459 amino acids
(B) TYPE: amino acid
(C) STRANDEDNESS: single
(D) TOPOLOGY: linear (xi) SEQUENCE DESCRIPTION: SEQ ID NO:2:

```
Met Lys Lys Phe Asn Gln Ser Leu Leu Ala Thr Ala Met Leu Leu Ala
1               5                   10                  15

Ala Gly Gly Ala Asn Ala Ala Ala Phe Gln Leu Ala Glu Val Ser Thr
            20                  25                  30

Ser Gly Leu Gly Arg Ala Tyr Ala Gly Glu Ala Ala Ile Ala Asp Asn
        35                  40                  45

Ala Ser Val Val Ala Thr Asn Pro Ala Leu Met Ser Leu Phe Lys Thr
    50                  55                  60

Ala Gln Phe Ser Thr Gly Gly Val Tyr Ile Asp Ser Arg Ile Asn Met
65                  70                  75                  80

Asn Gly Asp Val Thr Ser Tyr Ala Gln Ile Ile Thr Asn Gln Ile Gly
                85                  90                  95

Met Lys Ala Ile Lys Asp Gly Ser Ala Ser Gln Arg Asn Val Val Pro
            100                 105                 110

Gly Ala Phe Val Pro Asn Leu Tyr Phe Val Ala Pro Val Asn Asp Lys
        115                 120                 125

Phe Ala Leu Gly Ala Gly Met Asn Val Asn Phe Gly Leu Lys Ser Glu
    130                 135                 140

Tyr Asp Asp Ser Tyr Asp Ala Gly Val Phe Gly Gly Lys Thr Asp Leu
145                 150                 155                 160

Ser Ala Ile Asn Leu Asn Leu Ser Gly Ala Tyr Arg Val Thr Glu Gly
                165                 170                 175

Leu Ser Leu Gly Leu Gly Val Asn Ala Val Tyr Ala Lys Ala Gln Val
            180                 185                 190
```

-continued

```
Glu Arg Asn Ala Gly Leu Ile Ala Asp Ser Val Lys Asp Asn Gln Ile
        195                 200                 205

Thr Ser Ala Leu Ser Thr Gln Gln Glu Pro Phe Arg Asp Leu Lys Lys
    210                 215                 220

Tyr Leu Pro Ser Lys Asp Lys Ser Val Val Ser Leu Gln Asp Arg Ala
225                 230                 235                 240

Ala Trp Gly Phe Gly Trp Asn Ala Gly Val Met Tyr Gln Phe Asn Glu
                245                 250                 255

Ala Asn Arg Ile Gly Leu Ala Tyr His Ser Lys Val Asp Ile Asp Phe
            260                 265                 270

Ala Asp Arg Thr Ala Thr Ser Leu Glu Ala Asn Val Ile Lys Glu Gly
        275                 280                 285

Lys Lys Gly Asn Leu Thr Phe Thr Leu Pro Asp Tyr Leu Glu Leu Ser
    290                 295                 300

Gly Phe His Gln Leu Thr Asp Lys Leu Ala Val His Tyr Ser Tyr Lys
305                 310                 315                 320

Tyr Thr His Trp Ser Arg Leu Thr Lys Leu His Ala Ser Phe Glu Asp
                325                 330                 335

Gly Lys Lys Ala Phe Asp Lys Glu Leu Gln Tyr Ser Asn Asn Ser Arg
            340                 345                 350

Val Ala Leu Gly Ala Ser Tyr Asn Leu Tyr Glu Lys Leu Thr Leu Arg
        355                 360                 365

Ala Gly Ile Ala Tyr Asp Gln Ala Ala Ser Arg His His Arg Ser Ala
    370                 375                 380

Ala Ile Pro Asp Thr Asp Arg Thr Trp Tyr Ser Leu Gly Ala Thr Tyr
385                 390                 395                 400

Lys Phe Thr Pro Asn Leu Ser Val Asp Leu Gly Tyr Ala Tyr Leu Lys
                405                 410                 415

Gly Lys Lys Val His Phe Lys Glu Val Lys Thr Ile Gly Asp Lys Arg
            420                 425                 430

Thr Leu Thr Leu Asn Thr Thr Ala Asn Tyr Thr Ser Gln Ala His Ala
        435                 440                 445

Asn Leu Tyr Gly Leu Asn Leu Asn Tyr Ser Phe
    450                 455
```

(2) INFORMATION FOR SEQ ID NO:3:

(i) SEQUENCE CHARACTERISTICS:
(A) LENGTH: 1365 base pairs
(B) TYPE: nucleic acid
(C) STRANDEDNESS: single
(D) TOPOLOGY: linear (xi) SEQUENCE DESCRIPTION: SEQ ID NO:3:

```
ATGAAAAAAT TTAATCAATC TATATTAGCA ACGGCAATGT TGTTGGCTGC AGGTGGTGCA     60

AATGCGGCAG CGTTTCAATT GGCGGAAGTT TCTACTTCAG GTCTTGGTCG TGCCTATGCA    120

GGTGAAGCGG CGATTGCAGA TAATGCTTCA GTGGTGGCAA CTAACCCAGC TTTGATGAGT    180

TTATTTAAAA CGGCACAGTT TTCCACAGGT GGCGTTTATG TTGATTCTAG AATTAATATG    240

AATGGTGATG TAACTGCTTC TATAGCAACT ACTAAAATGA ACTCAGCAAA GTACGGCTCA    300

GCTTCAGAGC GTAATGTTGT TCCTGGTGCT TTTGTGCCAA ATCTTTATTT CGTTGCTCCA    360

GTAAATGATA AATTCGCGCT GGGCGCAGGA ATGAATGTAA ATTTCGGTCT AAAAAGTGAA    420

TATGACGATA GTTATGATGC TGGTATATTT GGTGGAAAAA CGGACTTGAC TGCTATCAAC    480

TTAAATTTAA GTGGTGCTTA TCGAGTAACA GAAGGCTTGA GCCTAGGTTT AGGGGTAAAT    540
```

-continued

```
GCGGTTTATG CTAAAGCCCA AGTTGAACGG AATGCTGGTA TTATTGCGAA TAGTGTTAAT    600

GATACACAAG TAAAAACTGC ACTCTCAGTA CTGGCACCAC CACTCAAAGG GCTTGATCAG    660

AATTTGCCCT CTAAAGACAA ATCTGTTGTG TCATTACAAG ATAGAGCAGC TTGGGGGTTT    720

GGCTGGAATG CAGGTGTAAT GTATCAATTT AATGAAGCTA ACCGAATTGG TTTAGCTTAT    780

CATTCTAAAG TGGACATTGA TTTTACTGAC CGCACTGCCA CTAGTGTAGA AGCAAATGTC    840

ATCAAAGAAG GTAAAAAAGG TAATTTAACC CTTACATTGC CAGATTACTT AGAACTTTCT    900

GGGTTCCATC AATTAACTGA CAAATTTGCA GTGCATTATA GTTATAAATA TACCCATTGG    960

AGTCGTTTAA CAAAATTACA CGCTAGCTTC GAAGATGGTA AGAAAGCTTT TGATAAAGAA   1020

TTACAATACA GTAATAACTC TCGTGTTGCA TTAGGGGCAA GTTATAATCT TGATGAAAAA   1080

TTAACCTTAC GTGCGGGTAT TGCTTACGAT CAAGCTGCAT CTCGTCATCA CCGTAGTGCT   1140

GCAATTCCAG ATACCGATCG CACTTGGTAT AGTTTAGGTG CAACCTATAA ATTCACGCCG   1200

AATTTATCTG TTGATCTTGG CTATGCTTAC TTAAAAGGCA AAAAAGTTCA CTTTAAAGAA   1260

GTAAAAACAA TAGGTGACAA ACGTACATTG ACATTGAATA CAACTGCAAA TTATACTTCT   1320

CAAGCACACG CAAATCTTTA CGGTTTGAAT TTAAATTATA GTTTC                   1365
```

(2) INFORMATION FOR SEQ ID NO:4:

(i) SEQUENCE CHARACTERISTICS:
(A) LENGTH: 455 amino acids
(B) TYPE: amino acid
(C) STRANDEDNESS: single
(D) TOPOLOGY: linear (xi) SEQUENCE DESCRIPTION: SEQ ID NO:4:

```
Met Lys Lys Phe Asn Gln Ser Ile Leu Ala Thr Ala Met Leu Leu Ala
1               5                   10                  15

Ala Gly Gly Ala Asn Ala Ala Ala Phe Gln Leu Ala Glu Val Ser Thr
            20                  25                  30

Ser Gly Leu Gly Arg Ala Tyr Ala Gly Glu Ala Ala Ile Ala Asp Asn
        35                  40                  45

Ala Ser Val Val Ala Thr Asn Pro Ala Leu Met Ser Leu Phe Lys Thr
    50                  55                  60

Ala Gln Phe Ser Thr Gly Gly Val Tyr Val Asp Ser Arg Ile Asn Met
65                  70                  75                  80

Asn Gly Asp Val Thr Ala Ser Ile Ala Thr Thr Lys Met Asn Ser Ala
                85                  90                  95

Lys Tyr Gly Ser Ala Ser Glu Arg Asn Val Val Pro Gly Ala Phe Val
            100                 105                 110

Pro Asn Leu Tyr Phe Val Ala Pro Val Asn Asp Lys Phe Ala Leu Gly
        115                 120                 125

Ala Gly Met Asn Val Asn Phe Gly Leu Lys Ser Glu Tyr Asp Asp Ser
    130                 135                 140

Tyr Asp Ala Gly Ile Phe Gly Gly Lys Thr Asp Leu Thr Ala Ile Asn
145                 150                 155                 160

Leu Asn Leu Ser Gly Ala Tyr Arg Val Thr Glu Gly Leu Ser Leu Gly
                165                 170                 175

Leu Gly Val Asn Ala Val Tyr Ala Lys Ala Gln Val Glu Arg Asn Ala
            180                 185                 190

Gly Ile Ile Ala Asn Ser Val Asn Asp Thr Gln Val Lys Thr Ala Leu
        195                 200                 205

Ser Val Leu Ala Pro Pro Leu Lys Gly Leu Asp Gln Asn Leu Pro Ser
```

```
            210                 215                 220
Lys Asp Lys Ser Val Val Ser Leu Gln Asp Arg Ala Ala Trp Gly Phe
225                 230                 235                 240

Gly Trp Asn Ala Gly Val Met Tyr Gln Phe Asn Glu Ala Asn Arg Ile
                245                 250                 255

Gly Leu Ala Tyr His Ser Lys Val Asp Ile Asp Phe Thr Asp Arg Thr
                260                 265                 270

Ala Thr Ser Val Glu Ala Asn Val Ile Lys Glu Gly Lys Lys Gly Asn
            275                 280                 285

Leu Thr Leu Thr Leu Pro Asp Tyr Leu Glu Leu Ser Gly Phe His Gln
290                 295                 300

Leu Thr Asp Lys Phe Ala Val His Tyr Ser Tyr Lys Tyr Thr His Trp
305                 310                 315                 320

Ser Arg Leu Thr Lys Leu His Ala Ser Phe Glu Asp Gly Lys Lys Ala
                325                 330                 335

Phe Asp Lys Glu Leu Gln Tyr Ser Asn Asn Ser Arg Val Ala Leu Gly
                340                 345                 350

Ala Ser Tyr Asn Leu Asp Glu Lys Leu Thr Leu Arg Ala Gly Ile Ala
            355                 360                 365

Tyr Asp Gln Ala Ala Ser Arg His His Arg Ser Ala Ala Ile Pro Asp
370                 375                 380

Thr Asp Arg Thr Trp Tyr Ser Leu Gly Ala Thr Tyr Lys Phe Thr Pro
385                 390                 395                 400

Asn Leu Ser Val Asp Leu Gly Tyr Ala Tyr Leu Lys Gly Lys Lys Val
                405                 410                 415

His Phe Lys Glu Val Lys Thr Ile Gly Asp Lys Arg Thr Leu Thr Leu
                420                 425                 430

Asn Thr Thr Ala Asn Tyr Thr Ser Gln Ala His Ala Asn Leu Tyr Gly
            435                 440                 445

Leu Asn Leu Asn Tyr Ser Phe
450                 455

(2) INFORMATION FOR SEQ ID NO:5:

    (i) SEQUENCE CHARACTERISTICS:
        (A) LENGTH: 1347 base pairs
        (B) TYPE: nucleic acid
        (C) STRANDEDNESS: single
        (D) TOPOLOGY: linear

    (xi) SEQUENCE DESCRIPTION: SEQ ID NO:5:

ATGAAAAAAT TTAATCAATC TATATTAGCA ACAGCAATGT TGTTGGCTGC AGGTGGTGCA      60

AATGCGGCAG CGTTTCAATT GGCGGAAGTT TCTACTTCTG GGCTTGGTCG TGCCTATGCG     120

GGTGAAGCGG CGATTGCAGA TAATGCTTCT GTCGTGGCAA CTAACCCAGC TTTGATGAGT     180

TTATTTAAAA CGGCACAGTT TTCCACAGGT GGCGTTTATG TTGATTCTAG AATTAATATG     240

AATGGTGATG TAGCTGCTTC TATAAAAGGT GCTACAATGA ACACAACAAA GGACGGCTCA     300

GCTTCAGAGC GTAATGTTGT TCCTGGTGCT TTTGTGCCAA ATCTTTATTT CGTTGCTCCA     360

GTGAATGATA AATTAGCGGT GGGTGCAGGA ATGAATGTAA ATTTCGGTCT AAAAAGTAAA     420

TATGACGATA GTTATGATGC TGGTGTATTT GGTGGAAAAA CTGACTTGAC TGCTATCAAC     480

TTAAATTTAA GTGGTGCTTA TCGAGTAACA GAAGGCTTAA GCGTAGGTTT AGGGGTAAAT     540

GCGGTTTATG CTAAAGCCCA AGTTGAACGG AATGCTGGTA TTATTACGGA GAGTGTTAAG     600

ATTGCACAAA ACGCACTCAA AACAGTAGTT CCAGGAACAC CAATTCCTGA CTATTTGACC     660
```

-continued

```
TCTAAAAACA AGTCTGTTGT GTCATTACAA GATAGAGCAG CTTGGGGGTT TGGCTGGAAT    720

GCAGGTGTAA TGTATCAATT TAATGAAGGT AACCGAATTG GTTTAGCTTA TCATTCTAAA    780

GTGGACATTG ATTTTACTGA CCGCACTGCC ACTAGTTTAT ACGCAAATGT CATCAAAGAA    840

GGTAAAAAAG GTAATTTAAC CCTTAAATTG CCAGATTACT TAGAACTTTC TGGTTTCCAT    900

CAATTAACTG ACAAATTTGC TGTGCATTAT AGTTATAAAT ATACCCATTG GAGTCGTTTA    960

ACAAAATTAC ATGCTAGCTT CGAAGATGGT AAGAAAGCTT TTGATAAAGA ATTGCAATAC   1020

AGTAATAACT CTCGTATTGC ATTAGGGGCA AGTTATAATC TTGATGAAAA ATTGACCTTA   1080

CGTGCGGGTA TTGCTTACGA TCAAGCTGCA TCTCGTCATC ACCGTAGTGC TGCAATTCCA   1140

GATACCAATC GCACTTGGTA TAGTTTAGGG GCAACCTATA AATTCACGCC GAATTTATCT   1200

GTTGATCTTG GCTATGCTTA CTTAAAAGGC AAAAAAGTTC ACTTTAAAGA AGCACAACAA   1260

GCTGCAGGTG GCTTCATAAC AACAACCGCA AATTACACTT CTCAAGCACA CGCAAATCTT   1320

TACGGCTTAA ACTTAAATTA TAGTTTC                                       1347
```

(2) INFORMATION FOR SEQ ID NO:6:

(i) SEQUENCE CHARACTERISTICS:
(A) LENGTH: 432 amino acids
(B) TYPE: amino acid
(C) STRANDEDNESS: single
(D) TOPOLOGY: linear (xi) SEQUENCE DESCRIPTION: SEQ ID NO:6:

```
Met Lys Lys Phe Asn Gln Ser Ile Leu Ala Thr Ala Met Leu Leu Ala
1               5                   10                  15

Ala Gly Gly Ala Asn Ala Ala Ala Phe Gln Leu Ala Glu Val Ser Thr
            20                  25                  30

Ser Gly Leu Gly Arg Ala Tyr Ala Gly Glu Ala Ala Ile Ala Asp Asn
        35                  40                  45

Ala Ser Val Val Ala Thr Asn Pro Ala Leu Met Ser Leu Phe Lys Thr
    50                  55                  60

Ala Gln Phe Ser Thr Gly Gly Val Tyr Val Asp Ser Arg Ile Asn Met
65                  70                  75                  80

Asn Gly Asp Val Ala Ala Ser Ile Lys Gly Ala Thr Met Asn Thr Thr
                85                  90                  95

Lys Asp Gly Ser Ala Ser Glu Arg Asn Val Val Pro Gly Ala Phe Val
            100                 105                 110

Pro Asn Leu Tyr Phe Val Ala Pro Val Asn Asp Lys Leu Ala Val Gly
        115                 120                 125

Ala Gly Met Asn Val Asn Phe Gly Leu Lys Ser Lys Tyr Asp Asp Ser
    130                 135                 140

Tyr Asp Ala Gly Val Phe Gly Gly Lys Thr Asp Leu Thr Ala Ile Asn
145                 150                 155                 160

Leu Asn Leu Ser Gly Ala Tyr Arg Val Thr Glu Gly Leu Ser Val Gly
                165                 170                 175

Leu Gly Val Asn Ala Val Tyr Ala Lys Ala Gln Val Glu Arg Asn Ala
            180                 185                 190

Gly Ile Ile Thr Glu Ser Val Lys Ile Ala Gln Asn Ala Leu Lys Thr
        195                 200                 205

Val Val Pro Gly Thr Pro Ile Pro Asp Tyr Leu Thr Ser Lys Asn Lys
    210                 215                 220

Ser Val Val Ser Leu Gln Asp Arg Ala Ala Trp Gly Phe Gly Trp Asn
225                 230                 235                 240
```

-continued

```
Ala Gly Val Met Tyr Gln Phe Asn Glu Gly Asn Arg Ile Gly Leu Ala
                245                 250                 255

Tyr His Ser Lys Val Asp Ile Asp Phe Thr Asp Arg Thr Ala Thr Ser
            260                 265                 270

Leu Tyr Ala Asn Val Ile Lys Glu Gly Lys Lys Gly Asn Leu Thr Leu
        275                 280                 285

Lys Leu Pro Asp Tyr Leu Glu Leu Ser Gly Phe His Gln Leu Thr Asp
    290                 295                 300

Lys Phe Ala Val His Tyr Ser Tyr Lys Tyr Thr His Trp Ser Arg Leu
305                 310                 315                 320

Thr Lys Leu His Ala Ser Phe Glu Asp Gly Lys Lys Ala Phe Asp Lys
                325                 330                 335

Glu Leu Gln Tyr Ser Asn Asn Ser Arg Ile Ala Leu Gly Ala Ser Tyr
            340                 345                 350

Asn Leu Asp Glu Lys Leu Thr Leu Arg Ala Gly Ile Ala Tyr Asp Gln
        355                 360                 365

Ala Ala Ser Arg His His Arg Ser Ala Ala Ile Pro Asp Thr Asn Arg
    370                 375                 380

Thr Trp Tyr Ser Leu Gly Ala Thr Tyr Lys Phe Thr Pro Asn Leu Ser
385                 390                 395                 400

Val Asp Leu Gly Tyr Ala Tyr Leu Lys Gly Lys Lys Val His Phe Lys
                405                 410                 415

Glu Ala Gln Gln Ala Ala Gly Gly Phe Ile Thr Thr Thr Ala Asn Tyr
            420                 425                 430
```

(2) INFORMATION FOR SEQ ID NO:7:

(i) SEQUENCE CHARACTERISTICS:
(A) LENGTH: 48 base pairs
(B) TYPE: nucleic acid
(C) STRANDEDNESS: single
(D) TOPOLOGY: linear (xi) SEQUENCE DESCRIPTION: SEQ ID NO:7:

```
ATGAAAGGGG GAATTCTGTC CCTGCTGGTT CCAGCTCTGC TGGCTGCA                  48
```

(2) INFORMATION FOR SEQ ID NO:8:

(i) SEQUENCE CHARACTERISTICS:
(A) LENGTH: 48 base pairs
(B) TYPE: nucleic acid
(C) STRANDEDNESS: single
(D) TOPOLOGY: linear (xi) SEQUENCE DESCRIPTION: SEQ ID NO:8:

```
ATGAAAGTTA AAGTACTGTC CCTGCTGGTT CCAGCTCTGC TGGCTGCA                  48
```

(2) INFORMATION FOR SEQ ID NO:9:

(i) SEQUENCE CHARACTERISTICS:
(A) LENGTH: 21 amino acids
(B) TYPE: amino acid
(C) STRANDEDNESS: single
(D) TOPOLOGY: linear (xi) SEQUENCE DESCRIPTION: SEQ ID NO:9:

```
Met Lys Gly Gly Ile Leu Ser Leu Leu Val Pro Ala Leu Leu Ala Ala
1               5                   10                  15

Gly Gly Ala Asn Ala
            20
```

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:10:

```
Met Lys Val Lys Val Leu Ser Leu Leu Val Pro Ala Leu Leu Ala Ala
 1               5                  10                  15

Gly Gly Ala Asn Ala
             20
```

(2) INFORMATION FOR SEQ ID NO:11:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (xi) SEQUENCE DESCRIPTION: SEQ ID NO:11:

```
AGTGCTGCAA TTCCAGATAC CGATCGCACT TGGTATAGTT TAGGTGCAAC CTATAAATTC      60

ACGCCGAATT TATCTGTTGA TCTTGGCTAT GCTTACTTAA AAGGCAAAAA AGTTCACTTT     120

AAAGAAGTAA AAACAATAGG TGACAAACGT ACATTGACAT TGAATACAAC TGCAAATTAT     180

ACTTCTCAAG CACACGCAAA TCTTTACGGT TTGAATTTAA ATTATAGTTT CTAATCCGTT     240
```

(2) INFORMATION FOR SEQ ID NO:12:

(i) SEQUENCE CHARACTERISTICS:
        (A) LENGTH: 77 amino acids
        (B) TYPE: amino acid
        (C) STRANDEDNESS: single
        (D) TOPOLOGY: linear (xi) SEQUENCE DESCRIPTION: SEQ ID NO:12:

```
Ser Ala Ala Ile Pro Asp Thr Asp Arg Thr Trp Tyr Ser Leu Gly Ala
 1               5                  10                  15

Thr Tyr Lys Phe Thr Pro Asn Leu Ser Val Asp Leu Gly Tyr Ala Tyr
                20                  25                  30

Leu Tyr Gly Lys Lys Val His Phe Lys Glu Val Lys Thr Ile Gly Asp
             35                  40                  45

Lys Arg Thr Leu Thr Leu Asn Thr Thr Ala Asn Tyr Thr Ser Gln Ala
         50                  55                  60

His Ala Asn Leu Tyr Gly Leu Asn Leu Asn Tyr Ser Phe
65                  70                  75
```

(2) INFORMATION FOR SEQ ID NO:13:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:13:

```
Ala Ala Phe Gln Leu Ala Glu Val Ser Thr Ser Gly Leu Gly Arg Ala
 1               5                  10                  15

Tyr Ala Gly Glu Ala Ala Ile Ala Asp Asn Ala Ser Val
                20                  25
```

(2) INFORMATION FOR SEQ ID NO:14:

(i) SEQUENCE CHARACTERISTICS:
(A) LENGTH: 29 amino acids
(B) TYPE: amino acid
(C) STRANDEDNESS: single
(D) TOPOLOGY: linear (xi) SEQUENCE DESCRIPTION: SEQ ID NO:14:

```
Gly Asp Val Thr Ser Tyr Ala Gln Ile Ile Thr Asn Gln Ile Gly Met
1               5                   10                  15

Lys Ala Ile Lys Asp Gly Ser Ala Ser Gln Arg Asn Val
            20                  25
```

(2) INFORMATION FOR SEQ ID NO:15:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:15:

```
Val Asn Asp Lys Phe Ala Leu Gly Ala Gly Met Asn Val Asn Phe Gly
1               5                   10                  15

Leu Lys Ser Glu Tyr Asp Asp Ser Tyr Asp Ala Gly Val Phe Gly Gly
            20                  25                  30

Lys Thr Asp
        35
```

(2) INFORMATION FOR SEQ ID NO:16:

(i) SEQUENCE CHARACTERISTICS:
(A) LENGTH: 29 amino acids
(B) TYPE: amino acid
(C) STRANDEDNESS: single
(D) TOPOLOGY: linear (xi) SEQUENCE DESCRIPTION: SEQ ID NO:16:

```
Tyr Ala Lys Ala Gln Val Glu Arg Asn Ala Gly Leu Ile Ala Asp Ser
1               5                   10                  15

Val Lys Asp Asn Gln Ile Thr Ser Ala Leu Ser Thr Gln
            20                  25
```

(2) INFORMATION FOR SEQ ID NO:17:

(i) SEQUENCE CHARACTERISTICS:
(A) LENGTH: 29 amino acids
(B) TYPE: amino acid
(C) STRANDEDNESS: single
(D) TOPOLOGY: linear (xi) SEQUENCE DESCRIPTION: SEQ ID NO:17:

```
Ala Leu Ser Thr Gln Gln Glu Phe Arg Asp Leu Lys Lys Tyr Leu Pro
1               5                   10                  15

Ser Lys Asp Lys Ser Val Val Ser Leu Gln Asp Arg Ala
            20                  25
```

(2) INFORMATION FOR SEQ ID NO:18:

(i) SEQUENCE CHARACTERISTICS:
(A) LENGTH: 28 amino acids
(B) TYPE: amino acid
(C) STRANDEDNESS: single
(D) TOPOLOGY: linear (xi) SEQUENCE DESCRIPTION: SEQ ID NO:18:

```
Ala Gly Val Met Tyr Gln Phe Asn Glu Ala Asn Arg Ile Gly Leu Ala
1               5                   10                  15

Tyr His Ser Lys Val Asp Ile Asp Phe Ala Asp Arg
            20                  25
```

(2) INFORMATION FOR SEQ ID NO:19:

(i) SEQUENCE CHARACTERISTICS:
(A) LENGTH: 36 amino acids
(B) TYPE: amino acid
(C) STRANDEDNESS: single
(D) TOPOLOGY: linear (xi) SEQUENCE DESCRIPTION: SEQ ID NO:19:

```
Ile Asp Phe Ala Asp Arg Thr Ala Thr Ser Leu Glu Ala Asn Val Ile
1               5                   10                  15

Lys Glu Gly Lys Lys Gly Asn Leu Thr Phe Thr Leu Pro Asp Tyr Leu
            20                  25                  30

Glu Leu Ser Gly
        35
```

(2) INFORMATION FOR SEQ ID NO:20:

(i) SEQUENCE CHARACTERISTICS:
(A) LENGTH: 34 amino acids
(B) TYPE: amino acid
(C) STRANDEDNESS: single
(D) TOPOLOGY: linear (xi) SEQUENCE DESCRIPTION: SEQ ID NO:20:

```
Leu Glu Leu Ser Gly Phe His Gln Leu Thr Asp Lys Leu Ala Val His
1               5                   10                  15

Tyr Ser Tyr Lys Tyr Thr His Trp Ser Arg Leu Thr Lys Leu His Ala
            20                  25                  30

Ser Phe
```

(2) INFORMATION FOR SEQ ID NO:21:

(i) SEQUENCE CHARACTERISTICS:
(A) LENGTH: 25 amino acids
(B) TYPE: amino acid
(C) STRANDEDNESS: single
(D) TOPOLOGY: linear (xi) SEQUENCE DESCRIPTION: SEQ ID NO:21:

```
Lys Leu His Ala Ser Phe Glu Asp Gly Lys Lys Ala Phe Asp Lys Glu
1               5                   10                  15

Leu Gln Tyr Ser Asn Asn Ser Arg Val
            20                  25
```

(2) INFORMATION FOR SEQ ID NO:22:

(i) SEQUENCE CHARACTERISTICS:
(A) LENGTH: 32 amino acids
(B) TYPE: amino acid
(C) STRANDEDNESS: single
(D) TOPOLOGY: linear (xi) SEQUENCE DESCRIPTION: SEQ ID NO:22:

```
Leu Tyr Glu Lys Leu Thr Leu Arg Ala Gly Ile Ala Tyr Asp Gln Ala
1               5                   10                  15

Ala Ser Arg His His Arg Ser Ala Ala Ile Pro Asp Thr Asp Arg Thr
            20                  25                  30
```

-continued

```
(2) INFORMATION FOR SEQ ID NO:23:

     (i) SEQUENCE CHARACTERISTICS:
          (A) LENGTH: 29 amino acids
          (B) TYPE: amino acid
          (C) STRANDEDNESS: single
          (D) TOPOLOGY: linear

    (xi) SEQUENCE DESCRIPTION: SEQ ID NO:23:

Leu Ser Val Asp Leu Gly Tyr Ala Tyr Leu Lys Gly Lys Lys Val His
1               5                   10                  15

Phe Lys Glu Val Lys Thr Ile Gly Asp Lys Arg Thr Leu
            20                  25


(2) INFORMATION FOR SEQ ID NO:24:

     (i) SEQUENCE CHARACTERISTICS:
          (A) LENGTH: 26 amino acids
          (B) TYPE: amino acid
          (C) STRANDEDNESS: single
          (D) TOPOLOGY: linear

    (xi) SEQUENCE DESCRIPTION: SEQ ID NO:24:

Leu Phe Lys Thr Ala Gln Phe Ser Thr Gly Gly Val Tyr Ile Asp Ser
1               5                   10                  15

Arg Ile Asn Met Asn Gly Asp Val Thr Ser
            20                  25


(2) INFORMATION FOR SEQ ID NO:25:

     (i) SEQUENCE CHARACTERISTICS:
          (A) LENGTH: 38 amino acids
          (B) TYPE: amino acid
          (C) STRANDEDNESS: single
          (D) TOPOLOGY: linear

    (xi) SEQUENCE DESCRIPTION: SEQ ID NO:25:

Phe Lys Glu Val Lys Thr Ile Gly Asp Lys Arg Thr Leu Thr Leu Asn
1               5                   10                  15

Thr Thr Ala Asn Tyr Thr Ser Gln Ala His Ala Asn Leu Tyr Gly Leu
            20                  25                  30

Asn Leu Asn Tyr Ser Phe
        35


(2) INFORMATION FOR SEQ ID NO:26:

     (i) SEQUENCE CHARACTERISTICS:
          (A) LENGTH: 35 amino acids
          (B) TYPE: amino acid
          (C) STRANDEDNESS: single
          (D) TOPOLOGY: linear

    (xi) SEQUENCE DESCRIPTION: SEQ ID NO:26:

Phe Lys Glu Ala Gln Gln Ala Ala Gly Gly Phe Ile Thr Thr Thr Ala
1               5                   10                  15

Asn Tyr Thr Ser Gln Ala His Ala Asn Leu Tyr Gly Leu Asn Leu Asn
            20                  25                  30

Tyr Ser Phe
        35
```